(12) United States Patent
Jamalabadi et al.

(10) Patent No.: US 7,063,784 B2
(45) Date of Patent: Jun. 20, 2006

(54) PROCESSING OF CHEMICALS IN FLOW-THROUGH DEVICE WITH POROUS MEDIA

(75) Inventors: Shahnaz Ghassemi Jamalabadi, Charlottesville, VA (US); Peter C. Rahn, Palmyra, VA (US); Kelvin J. Hammond, Charlottesville, VA (US); Omar Mneimne, Charlottesville, VA (US); Jeffrey A. Horsman, Charlottesville, VA (US); Peter C. Van Davelaar, Glen Allen, VA (US)

(73) Assignee: Biotage AB, Charlottesville, VA (US)

( * ) Notice: Subject to any disclaimer, the term of this patent is extended or adjusted under 35 U.S.C. 154(b) by 183 days.

(21) Appl. No.: 10/736,338

(22) Filed: Dec. 15, 2003

(65) Prior Publication Data
US 2004/0188354 A1   Sep. 30, 2004

Related U.S. Application Data

(63) Continuation-in-part of application No. 10/321,229, filed on Dec. 17, 2002, now abandoned, which is a continuation-in-part of application No. 10/136,131, filed on May 1, 2002, now Pat. No. 6,649,051.

(51) Int. Cl.
*B01D 15/08* (2006.01)

(52) U.S. Cl. .................. 210/198.2; 210/243; 210/656; 210/748; 422/70

(58) Field of Classification Search ................ 210/635, 210/656, 659, 198.2, 232, 238, 243, 282; 96/101, 105, 106; 422/70
See application file for complete search history.

(56) References Cited

U.S. PATENT DOCUMENTS

| 4,204,423 A | 5/1980 | Jordan ....................... 73/23.25 |
| 4,457,846 A | 7/1984 | Munk et al. |
| 5,549,819 A | 8/1996 | Nickerson ................ 210/198.2 |
| 6,139,733 A | 10/2000 | Hargro et al. ........... 210/198.2 |
| 6,416,716 B1 | 7/2002 | Shukla et al. ............... 422/101 |
| 6,423,120 B1 | 7/2002 | Nickerson et al. ............. 95/87 |
| 6,530,260 B1 | 3/2003 | Mustacich et al. ......... 73/23.41 |
| 6,541,272 B1 | 4/2003 | Mitra ......................... 436/178 |
| 6,649,051 B1 * | 11/2003 | Jamalabadi et al. ..... 210/198.2 |
| 2002/0132119 A1 | 9/2002 | Kirkland et al. |
| 2003/0109053 A1 | 6/2003 | Stone ......................... 436/161 |
| 2003/0205455 A1 | 11/2003 | Ghassemi et al. |

FOREIGN PATENT DOCUMENTS

| DE | 4031020 A1 | 4/1992 |
| EP | 0073176 A | 3/1983 |
| WO | WO 00/10676 | 3/2000 |

OTHER PUBLICATIONS

Information from Personal Chemistry website www.personalchemistry.com undated pp. 1-6.
Information from CEM website www.CEM.com undated pp. 1-15.
Information from Milestone, Inc. website www.milestonesci.com/SYN%Features.htm pp. 1-14 Aug. 30, 2002.

(Continued)

*Primary Examiner*—Ernest G. Therkorn
(74) *Attorney, Agent, or Firm*—Fish & Richardson P.C.

(57) ABSTRACT

A method of processing a sample comprising introducing a sample into a flow-through device containing a porous solid media therein, and thereafter subjecting the device to microwave energy.

12 Claims, 4 Drawing Sheets

OTHER PUBLICATIONS

Kaldor et al., "Use of Solid Supported 5-22 Nucleophiles and Electrophiles for the Purification of Non-Peptide Small Molecule Libraries", Tetrahedron Letters, vol. 37:7193-7196 (1996).

Tempest et al., "MCC/$S_n$ Ar Methodology, Part 1: Novel Access to a Range of Heterocyclic Cores," Tetrahedron Letters, vol. 42:4963-4968 (2001).

* cited by examiner

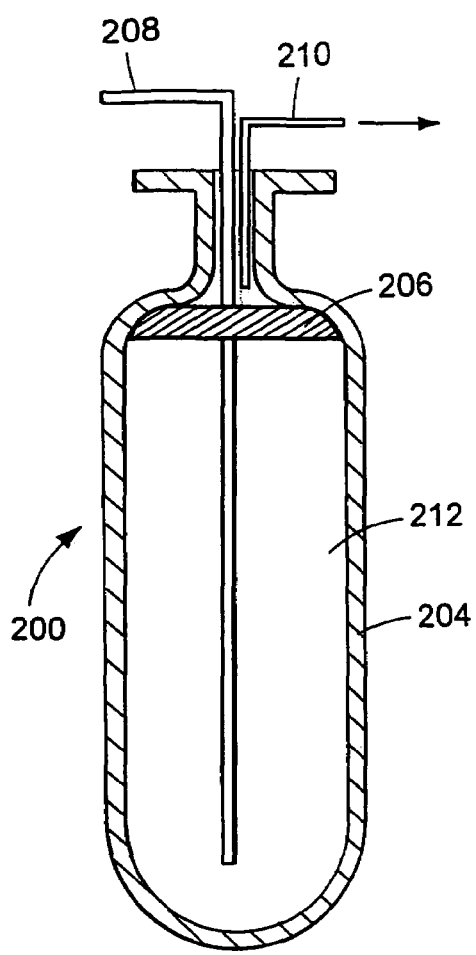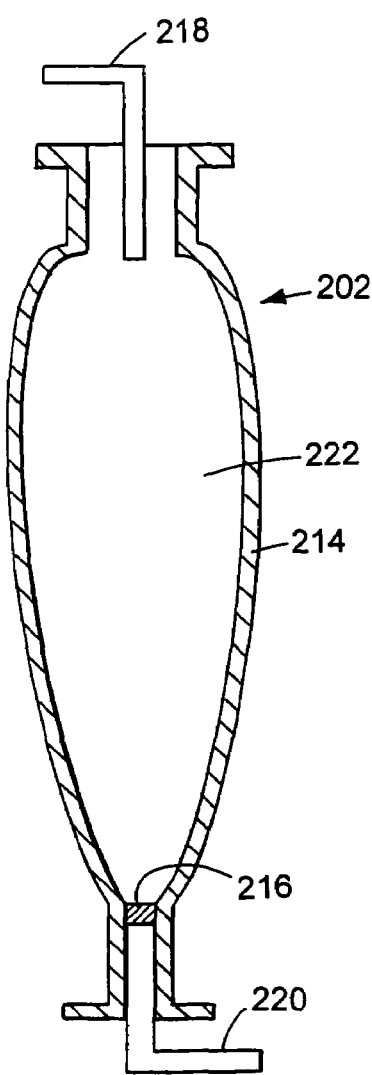
FIG. 10
FIG. 11

PROCESSING OF CHEMICALS IN FLOW-THROUGH DEVICE WITH POROUS MEDIA

This is a continuation-in-part of U.S. application Ser. No. 10/321,229, filed Dec. 17, 2002 now abandoned, which is a continuation-in-part of U.S. application Ser. No. 10/136,131, filed May 1, 2002, now U.S. Pat. No. 6,649,051.

TECHNICAL FIELD

The invention relates to processing of chemicals in flow-through devices with porous media.

U.S. Pat. No. 6,139,733, which is hereby incorporated by reference, describes a sample module made of a flow-through device that contains porous media and describes adding a chemical sample to the module prior to connecting the module to (or inserting the module into) a chromatography column. The sample can be added to the module in a dissolution solvent that can be removed by vacuum or heat prior to connection to the chromatography column.

SUMMARY

In one aspect, the invention features, in general, processing a chemical sample by introducing a sample into a flow-through device containing a porous solid media therein, and thereafter subjecting the device to a radiated energy source such as microwave energy, ultra-violet energy, sonic energy or other means to introduce energy into the device.

In another aspect, the invention features, in general, introducing a chemical sample into a flow-through device containing a porous solid media therein and active components attached to the solid media, and thereafter subjecting the device to energy in order to accelerate or promote reactions implemented by the active components, the reactions resulting in a reaction product created from the sample.

In another aspect, the invention features, in general, introducing reagents into a flow-through device containing a porous solid media therein and active components attached to the solid media, causing a chemical reaction involving the reagents in the flow-through device and resulting in a reaction product, thereafter placing the flow-through device into an entrance region within a chromatography column, and thereafter carrying out chromatography on the reaction product.

In another aspect, the invention features, in general a chromatography sample module including a flow-through member having walls and having an inlet end and an outlet end; a solid porous media disposed within the flow-through member and including attached active components, the media being spaced from the inlet end so that the walls extend above the media and so that the flow-through member defines a receiving region adapted to receive a head piece; and a sample carried on the media.

In another aspect, the invention features, in general, a tubular member that is sized to fit entirely within the end of a chromatography column containing a separation media, the module having an inlet and an outlet, and solid porous media within the tubular member and spaced from the inlet, so that the tubular member defines a receiving region adapted to receive a head piece. The tubular member is sized to be sealed within the chromatography column with a sealing device used to seal the chromatography column. The solid porous media includes attached active components and carries a sample.

In another aspect, the invention features, in general a flow-through device having walls and having an inlet end and an outlet end; a solid porous media disposed within the flow-through device including attached active components, the media being spaced from the inlet end so that the walls extend above the media and so that the flow-through member defines a receiving region adapted to receive a head piece; and a sample carried on the media.

In another aspect, the invention features, in general, a sample module including a tubular member that is sized to fit entirely within the end of a chromatography column containing a separation media, the module having an inlet and an outlet, and solid porous media within the tubular member. The solid porous media includes attached active components and carries a sample.

In another aspect, the invention features, in general a sample module including a flow-through device having walls and having an inlet end and an outlet end; a solid porous media disposed within the flow-through device including attached active components; and a sample carried on the media.

In another aspect, the invention features a method of processing a sample including introducing a sample into a flow-through device, subjecting the flow-through device and the sample therein to a radiated energy source while causing a change to the sample, and flowing liquid through the flow-through device to carry the sample to a chromatography column.

In another aspect the invention features s system for processing a sample including a flow-through device for receiving the sample therein, a radiated energy source receiving the flow-through device and the sample to apply radiated energy to the flow-through device and the sample while causing a change to the sample, and a chromatography column connectable to the flow-through device to receive the sample therefrom.

Particular embodiments of the invention may include one or more of the following features. In particular embodiments, the sample is introduced into the flow-through device in a solvent that is evaporated by microwave energy prior to carrying out chromatography. In some embodiments, the solid media includes active components attached thereto, and the microwave energy speeds up the reactions involving the active components. In some embodiments the sample includes reagents that undergo a chemical reaction to form a reaction product. The active components attached to the solid media can include scavengers to remove excess reagents. The scavengers can be electrophile scavengers, e.g., amino scavengers, $TsNHNH_2$ scavengers, or SH scavengers. The scavengers can be nucleophile scavengers, e.g., TsCl scavengers and NCO scavengers. The scavengers can be base scavengers, e.g., a quaternary amine scavenger. The scavengers can be acid scavengers, e.g., TsOH scavengers or COOH scavengers. The active components can be coupling agents, e.g., DCC coupling agents, HOBt coupling agents, or NHS coupling agents. The active components can be a catalyst, e.g., TsOH. The active components can be a catalyst remover, e.g., DEAM.

Particular embodiments can also involve a flow-through device with porous or solid (e.g., beads with attached active components) media including attached active components therein, or a flow-through device without media. The flow-through device can be connected to the chromatography column by an outflow line from the flow-through device to a chromatography column. The outflow line can be directly connected to the flow-through device, or can be connected to a holder that receives the flow-through device.

Embodiments of the invention may include one or more of the following advantages. The use of microwave energy to evaporate solvent in a flow-through device in which a sample carried in a solvent has been absorbed onto solid media in the flow through device greatly speeds up and simplifies the evaporation process. Attaching active components to the solid media in a flow-through device that can be used to introduce a sample into a chromatography column, permits the same device to be used as a reaction chamber and sample introduction device, simplifying and speeding up synthesis and purification. Subjecting the device with solid media and attached active components to microwave or other energy speeds up the synthesis or other reactions therein.

Other features and advantages of the invention will be apparent from the following detailed description and from the claims.

DESCRIPTION OF DRAWINGS

FIG. 10 is a diagrammatic vertical sectional view of a further alternative embodiment of a flow-through device.

FIG. 11 is a diagrammatic vertical sectional view of a further alternative embodiment of a flow-through device.

DETAILED DESCRIPTION

Figure 1:
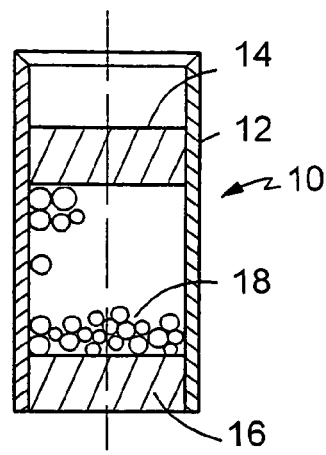
FIG. 1 is a FIG. 1 is a diagrammatic vertical sectional view of a flow-through device with a porous media therein.

Referring to FIG. 1, there is shown flow-through device 10, which includes cylindrical tube 12, porous plates 14, 16 (made of inert plastic porous frits or glass or Teflon), and porous solid media 18 (only partially shown in the figures) between porous plates 14, 16. Tube 12 can be made from glass, polyethylene, polypropylene, Teflon and other plastics. Media 18 can take various forms depending on the application. Media 18 can be silica, other conventional chromatography media, or solid media that has attached active components such as scavengers, coupling agents, catalysts, or catalyst removers.

Figure 2:
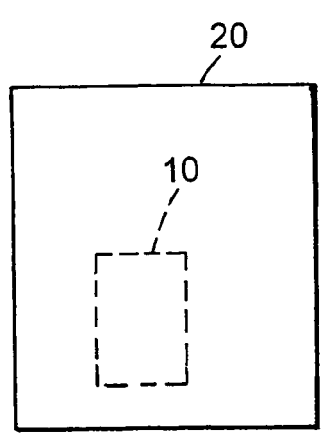
FIG. 2 is a diagrammatic view showing processing a sample in the FIG. 1 device in a microwave chamber.

Referring to FIG. 2, flow-through device 10, containing a sample to be processed therein, is shown being subjected to microwave energy in microwave chamber 20. In some applications, the processing involves removal of a dissolution solvent in which a sample compound of interest is dissolved. In other applications, the media plays an active role in chemical reactions taking place in the flow-through device. In some applications a conventional microwave oven can be used as the microwave chamber. In some other applications, it is better to use a microwave chamber with more precise controls, e.g., units available from Personal Chemistry, CEM or Milestone, Inc. (Monroe, Conn.).

Use of Flow-Through Device 10 for Removal of Dissolution Solvent

As is described in the above-referenced patent, when chemists optimize liquid chromatographic separations conditions, they may need to dissolve the sample mixture in a dissolution solvent which may be nonideal for elution. This can result in poor separation and poor recovery of desired components in a chromatography column. For example, polar solvents such as methanol, isopropanol (IPA), acetone, and ethylacetate (EtOAc) can interfere with chromatographic purification. The above-referenced patent describes adding a sample dissolved in a dissolution solvent to the top of the flow-through device (referred to as a sample module in the patent), where it is drawn into the media by capillary action. The sample absorbs onto the media, and the dissolution solvent is then removed by placing the flow-through device in a vacuum chamber and/or applying heat prior to placing the device in, or otherwise connecting it to, a chromatography column.

In order to avoid the use of a vacuum chamber or heat and to accelerate the drying of the solvent, one can instead subject the sample to microwave energy in microwave chamber 20. For example, subjecting flow through devices available from Biotage under the Flash 12 trade designation and containing one ml of the solvents IPA, EtOAc, acetone, methanol, and dichloromethane (DCM) in a conventional microwave oven (power set at 30) for 60 seconds resulted in the following percentage evaporations respectively, 82%, 72%, 96%, 88% and 92%. In general, removal of 80% of the polar solvent eliminates the interference of the chromatographic separation. When one is using the microwave chamber and sample module solely for the purpose of removing a dissolution solvent prior to chromatography, one may wish to use an inert media (e.g., sea sand or diatomaceous earth) instead of silica, in order to minimize the possibility of hydrolyzing acid sensitive groups. When polar solvent is removed, sample retention is enhanced, compound resolution is improved and tighter elution bands result. There also are increased separation efficiencies, lower volume fractions and increased loading capacities.

Figure 3:
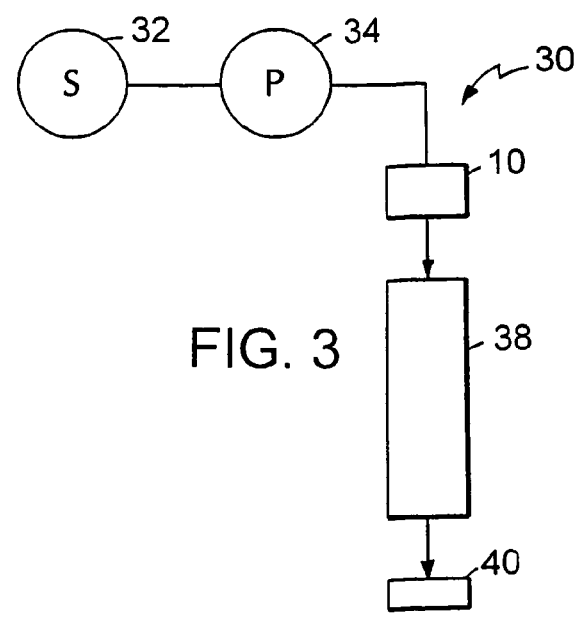
FIG. 3 is a schematic diagram showing subsequent use of the FIG. 1 device in a chromatography system.
Figure 4:
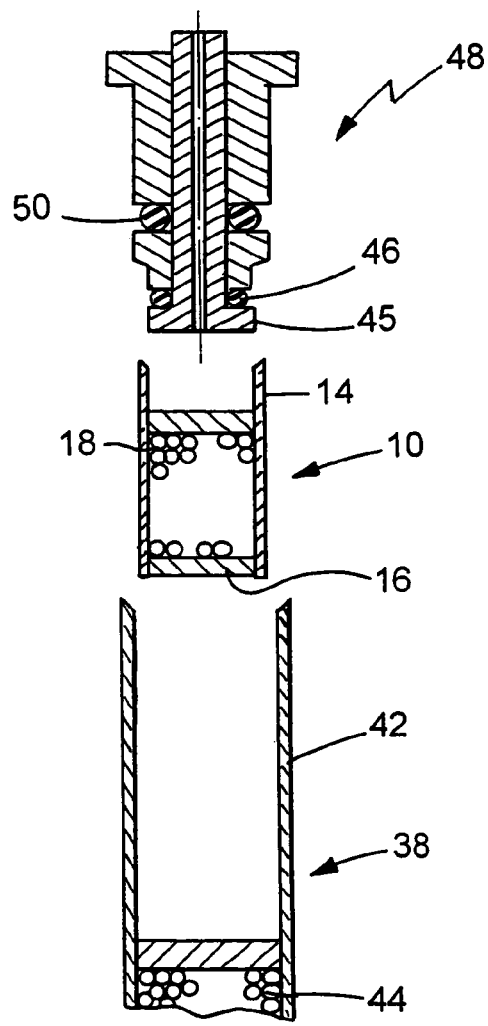
FIG. 4 shows how the FIG. 1 device fits within a chromatography column of the FIG. 3 chromatography system.

Referring to FIG. 3, flow-through device 10 (with a preabsorbed sample therein) is used in chromatography system 30, which also includes a source of solvent 32 (different than the polar dissolution solvent), pump 34, liquid chromatography column 38, and sample fraction collection system 40. In this system, solvent from source 32 is pumped by pump 34 through flow-through device 10 and chromatography column 38, carrying sample from device 10 thereto, to perform the chromatographic separation of the sample. FIG. 4 shows how flow-through device 10 is sized to fit entirely within the end 42 of chromatography column 38 containing a separation media 44. In device 10, the upper plate 14 is spaced from the upper end so that tubular member 12 defines a receiving region adapted to receive the lower end 45 and the lower compressible sealing ring 46 of sealing head piece 48, which also has an upper compressible sealing ring 50 for providing a seal to the chromatography column 38.

Figure 6:
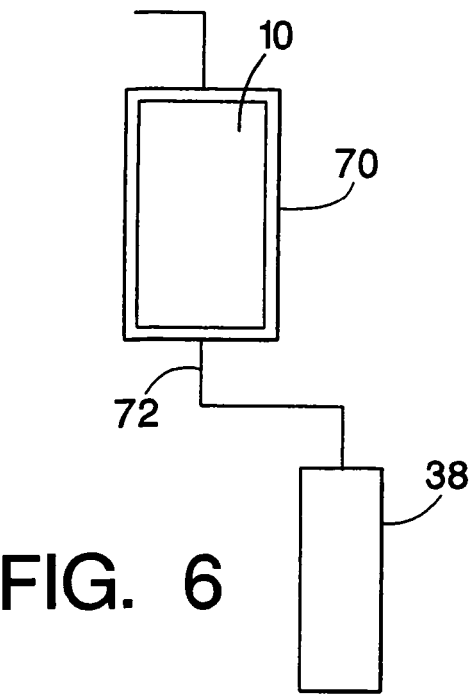
FIG. 6 is a schematic diagram showing subsequent use of the FIG. 1 device in an alternative arrangement in a chromatography system.

Alternatively, instead of inserting the device 10 into chromatography column 38, device can be placed in a remote holder 70 and connected to the chromatography column by a solvent tube 72, as shown in FIG. 6. Solvent could also be added to device 10, which is then placed directly into column 38, or remote holder 70 connected to chromatography column 38 by tube 72.

Figure 7:
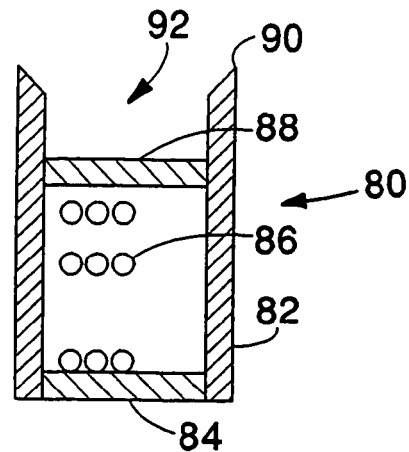
FIG. 7 is a diagrammatic vertical sectional view of an alternative embodiment of a flow-through device with a porous media therein.
Figure 8:
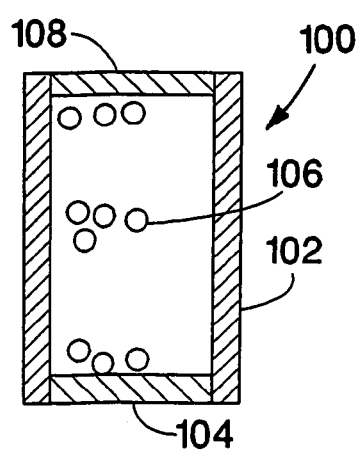
FIG. 8 is a diagrammatic vertical sectional view of a second alternative embodiment of a flow-through device with a porous media therein.
Figure 9:
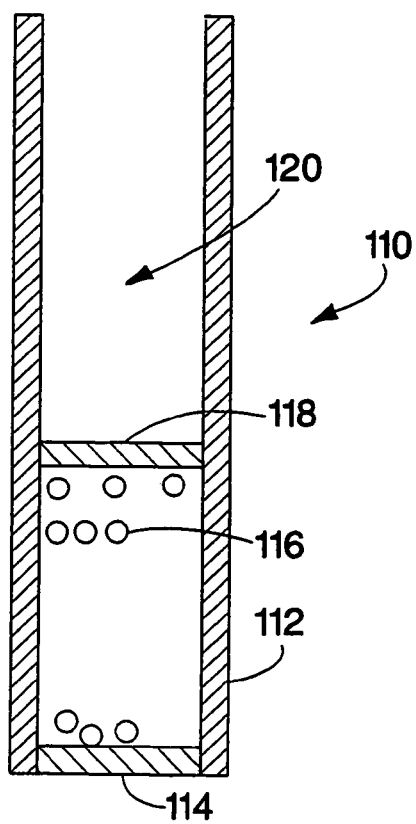
FIG. 9 is a diagrammatic vertical sectional view of a third alternative embodiment of a flow-through device with a porous media therein.

Device 10 can also be implemented in different forms, as shown in FIGS. 7–9.

Referring to FIG. 7, flow-through device 80 includes short plastic tube 82, which has a lower inert plastic porous frit 84 inserted so as to be flush with the bottom of tube 82. Tube 82 is then filled with a solid support 86 (e.g., porous media) to a pre-determined fill level, and a second inert plastic porous frit 88 is inserted. In this embodiment this top frit 88 is not flush with the top of the tube 82 and holds the solid support 86 in a stable form during shipping and ensures "plug flow" during use. In this embodiment the tube has a chamfer 90 on the top edge which eases insertion of both lower and upper frits 84, 88. In this case where the upper porous frit 88 is below the top of the tube 82, frit 88 may or may not form a sealing region 92 to allow a sealing head to be inserted which may or may-not be in contact with the top frit.

Referring to FIG. 8, flow-through device 100 includes short plastic tube 102, which has a lower inert plastic porous frit 104 inserted so as to be flush with the bottom of the tube 102. Tube 102 is then filled with a solid support 106 (e.g., porous media) to a pre-determined fill level, and a second inert plastic porous frit 108 is inserted. In this embodiment this top frit 108 is flush with the top of the tube 102 and holds the solid support 106 in a stable form during shipping and ensures "plug flow" during use.

Referring to FIG. 9, flow-through device 110 includes a longer plastic tube 112, which has a lower inert porous frit 114 inserted so as to be flush with the bottom of the tube 112. The tube is then filled with a solid support 116 (e.g., porous media) to as pre-determined fill level, and a second inert plastic porous frit 118 is inserted. In this embodiment this top frit 118 is not flush with the top of the tube 112 and holds the solid support 116 in a stable form during shipping and ensures "plug flow" during use. In this embodiment the tube 112 has a liquid receiving region 120 to enable wash solvent to be added after the liquid reaction has been absorbed.

Use of Flow-Through Device 10 as a Reaction Chamber

Flow-through device 10 can also be used as a reaction chamber in which the solid media includes attached active components such as scavengers, coupling agents, catalysts, or catalyst removers that assist in a chemical reaction therein. In this application, device 10 serves as a reaction chamber for solid phase organic synthesis (SPOS) or solid-assisted synthesis (SAS). In typical SPOS, a desired product (e.g., a small organic molecule being created as part of a combinatorial library) is synthesized on a bed; reactants and excess reagent stay in solution, and, at the end of the synthesis process, the excess reagents are washed out. In typical SAS, solid supports are used to hold reagents, catalysts for synthesis or chemoselective scavengers used to remove excess reactants during purification; this approach when applied to solution phase typically requires a long time for completion and involves many manual steps including washing and extractions.

Figure 5:
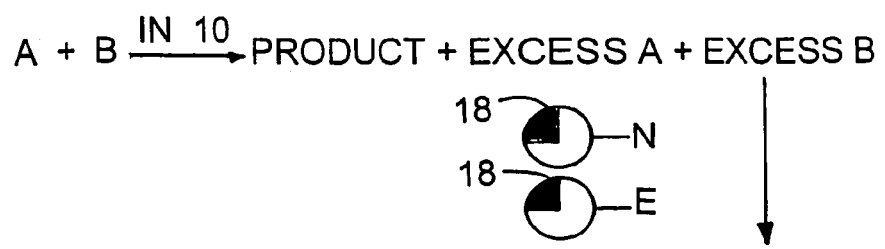
FIG. 5 illustrates reactions that can take place in the FIG. 1 device when it is used as a reaction device.

An example in which device 10 is used to facilitate scavenging of excess reagents is shown in FIG. 5. In this example, reagent A and reagent B are introduced into a flow-through device 10 that includes solid media 18 with attached nucleophile scavengers N and attached electrophile scavengers E. Reagents A and B combine to form the Product, and excess reagent A and excess reagent B are removed by the scavengers, resulting in a Purified Product, which is removed from device 10 in liquid form. The reaction can take place at room temperature or be aided by application of microwave energy (in microwave chamber 20 in FIG. 2) or conventional heat (e.g., from a hot plate) or a UV lamp. The use of microwave energy is superior because it results in an extremely short reaction time. In a reaction arrangement where, following synthesis, the desired product is purified in a chromatography column, flow-through device 10 provides for ease of introduction of the sample into the chromatography column as described in the above-referenced patent. Where it is desired to remove solvent prior to purification in the chromatography column, microwave energy can also be used to provide fast solvent evaporation. By using microwave synthesis on chemical samples and/or reagents in flow-through device 10 (with or without microwave drying) and then directly connecting device 10 to chromatography column 38 for separation and purification, one can potentially synthesize and purify new compounds in less than one hour.

Examples of nucleophile scavengers N are TsCl scavengers and NCO scavengers. These scavengers can be used to remove excess nucleophiles including amine, hydrazine, alcohols and organometallics.

Examples of electrophile scavengers are amino scavengers, $TsNHNH_2$ scavengers, and SH scavengers. The amino scavengers can scavenge acid chloride, sulfonylchloride and isocyanates. The $TsNHNH_2$ scavengers can scavenge aldehydes and ketones. The SH scavengers can scavenge alkylating agents, ranging from octyl bromide to benzyl bromide. Other electrophile and nucleophile scavengers can be used.

In addition, base scavengers, e.g., quaternary amine, can be used as a general base to quench reactions, neutralize amine hydrochlorides or to scavenge a variety of acidic molecules like carboxylic acids or acidic phenols.

Also, acid scavengers, e.g., TsOH and COOH, can be used. E.g., solid media with attached TsOH can be used as an equivalent to the strong cation-exchange resin, Amberlyst A-15 (Rohm & Hass). The device 10 with TsOH attached to the solid media can be used for removal of basic compounds, e.g., primary, secondary and tertiary amine, by quaternary salt formation. Also it can be used for quenching reactions with aqueous or soluble organic acids and for Boc-deblocking by catch and release of amine derivatives.

Coupling agents, such as DCC, HOBt and NHS, can also be attached to solid media and used for the synthesis of amides and esters. A catalyst, e.g., TsOH can also be attached to a solid media and used as a catalyst for esterification.

A catalyst remover can also be attached. E.g., DEAM attached to a solid media is highly efficient in scavenging oxopilic inorganic and organometallic complexes, including those of boron, titanium and tin. This resin can be used to quench reactions and remove metallic reagents, catalysts or byproducts.

In addition to synthesis reactions, sample module 10 can be used to carry out other reactions, e.g., one or more of the following reactions:

i. Organometallic nucleophilic additions (e.g. Grignards, organocuprates, lithiates, etc.)
    ii. Electrophilic additions to carbon-carbon multiple bonds.
    iii. Sigmatropic rearrangements.
    iv. Cycloadditions.
    v. Thermal eliminations.
    vi. Reductions (including hydrogenations).
    vii. Oxidations.
    viii. Multi-component condensations.

ix. Functional group interconversions.
x. Unimolecular rearrangements.
xi. Reactions involving transition metals.
xii. Aromatic substitutions.
xiii. Free-radical reactions.
xiv. Reactions of carbonyl compounds.
xv. Nucleophilic substitution reactions.

The reactions already described, including those involving the various scavengers, coupling agents, catalysts and catalyst removers, can be promoted and accelerated by placing the device 10 with the indicated solid media and reagents in microwave chamber 20 and applying microwave energy. In addition, the efficiencies of the reactions are improved such that the amount of excess reagents needed can be reduced. Alternatively, the device can be subjected to other forms of energy, including other forms of radiated energy, to promote and accelerate the reactions.

Use of flow-through device 10 as described can eliminate the manual manipulation involved in cleaning up a sample through extractions and washing and also provides a convenient reaction vessel.

FIGS. 10 and 11 show further alternative flow-through devices 200, 202.

Referring to FIG. 10, flow-through device 200 includes a vessel 204 made of microwave transparent material (glass or plastic), a porous frit or screen 206 across vessel 204 at the top of the vessel, and inflow line 208, which extends to the bottom of vessel 204, and outflow line 210, which begins above porous frit or screen 206. The interior region 212 of vessel 204 may or may not include reactive media, which could be porous or solid. Inflow line 208 and outflow line 210 may or may not be made of microwave transparent material. In use, reagents are placed in device 200, which is then placed in a microwave oven (e.g., microwave chamber 20 in FIG. 2) and used as a reaction vessel during application of microwave energy. After reacting the reagents, an assembly including inflow line 208 and outflow line 210 is inserted into the top of vessel 204, with inflow line 208 passing through porous frit or screen 206. Inflow line 208 is connected to a source of solvent (e.g., source 32 in FIG. 3) and outflow line 210 is connected to a chromatography cartridge (e.g., column 38 in FIG. 3) and liquid is passed through inflow line 208, upward through region 212 and porous frit or screen 206 and out through outflow line 210 to the chromatography cartridge.

Referring to FIG. 11, flow-through device 202 includes a vessel 214 made of microwave transparent material (glass or plastic), a porous frit or screen 216 across vessel 214 at the bottom of the vessel, inflow line 218, which ends at the top of the vessel 214, and outflow line 220, which begins at the bottom of vessel 214 and passes out of the bottom of vessel 214. The interior region 222 of vessel 214 may or may not include reactive media, which could be porous or solid. In use, reagents are placed in device 202, which is then placed in a microwave oven and used as a reaction vessel during application of microwave energy. After reacting the reagents, inflow line 218 is inserted into the top of vessel 214, and outflow line 220 is connected to a chromatography cartridge, and liquid is passed through inflow line 218, downward through region 222 and porous frit or screen 216 and out through outflow line 220 to the chromatography cartridge.

Nonporous or porous media (e.g., solid beads coated with a reactive media) can be used in the embodiments of FIGS. 1–4 and 6–11. The vessels of all embodiments of FIGS. 1–4 and 6–11 (including tubular member 12) can be made of glass or other microwave transparent materials.

The device of FIG. 10 or 11 can also be utilized to react the samples in an appropriate solvent and then drive off the solvent using microwave or other energy prior to introducing a chromatographically suitable solvents. A polar solvent can be driven off using heat, and this can also be accomplished using the microwave as the source of energy that heats up the solvent.

Other embodiments of the invention are within the scope of the appended claims.

What is claimed is:

1. A system for processing a sample comprising
   a flow-through device receiving said sample therein,
   a radiated energy source receiving said flow-through device and said sample in said device to apply radiated energy to said flow-through device and said sample while causing a change to said sample, and
   a chromatography column connectable to said flow-through device to receive said sample therefrom.

2. The system of claim 1 wherein said flow-through device has porous or solid media including attached active components therein.

3. The system of claim 2 wherein said media comprises solid media.

4. The system of claim 3 wherein said solid media comprises beads.

5. The system of claim 1 wherein said radiated energy source provides microwave energy.

6. The system of claim 1 wherein said sample includes reagents that undergo a chemical reaction to form a reaction product.

7. The system of claim 1 wherein said flow-through device does not have media therein.

8. The system of claim 1 wherein said flow-through device is made of glass.

9. The system of claim 1 wherein said flow-through device is made of plastic.

10. The system of claim 1 further comprising an outflow line from said flow-through device to said chromatography column.

11. The system of claim 1 further comprising a holder receiving said flow-through device, said holder having an outflow line to said chromatography column.

12. The system of claim 1 wherein said chromatography column has a receiving region at an inlet area of said chromatography column for receiving said flow-through device.

* * * * *